United States Patent [19]

Yoshida et al.

[11] Patent Number: 5,750,090
[45] Date of Patent: May 12, 1998

[54] SILICA-CERIUM OXIDE COMPOSITE PARTICLES, METHOD FOR THE PREPARATION THEREOF AND RESIN COMPOSITION AND A COSMETIC COMPOSITION COMPOUNDED THEREWITH

[75] Inventors: Sakae Yoshida; Satomi Shinnumadate; Shinryo Yabe; Shigeyoshi Momose; Kiminori Hirai, all of Tokyo, Japan

[73] Assignees: Nippon Inorganic Colour & Chemical Co., Ltd.; Kose Corporation, both of Tokyo, Japan

[21] Appl. No.: 777,790

[22] Filed: Dec. 31, 1996

[30] Foreign Application Priority Data

May 27, 1996 [JP] Japan .................................. 8-132284

[51] Int. Cl.$^6$ ...................................................... A61K 7/42
[52] U.S. Cl. ............................................................ 424/59
[58] Field of Search ................................................ 424/59

[56] References Cited

U.S. PATENT DOCUMENTS 5,478,550  12/1995  Suzuki et al. ........................ 424/59

FOREIGN PATENT DOCUMENTS

7207251  1/1994  Japan .
61-45646  8/1994  Japan .

Primary Examiner—Terressa Mosley
Attorney, Agent, or Firm—Wenderoth, Lind & Ponack

[57] ABSTRACT

Proposed is a powder of silica-cerium oxide composite particles useful as an ultraviolet shielding agent in a resin composition or as a sunscreening agent in a cosmetic composition. The cerium oxide-based composite particles consist of cerium oxide and 5 to 60% by weight of amorphous silica calculated as $SiO_2$. The composite particles are prepared by the addition of sodium silicate and an inorganic acid to an aqueous slurry containing precipitates of cerium hydroxide so as to precipitate amorphous silica on the particles of cerium hydroxide followed by drying and calcination of the particles separated from the reaction mixture. Various formulations of cosmetic compositions compounded with the silica-cerium oxide composite particles are disclosed.

17 Claims, 4 Drawing Sheets

SILICA-CERIUM OXIDE COMPOSITE PARTICLES, METHOD FOR THE PREPARATION THEREOF AND RESIN COMPOSITION AND A COSMETIC COMPOSITION COMPOUNDED THEREWITH

BACKGROUND OF THE INVENTION

The present invention relates to silica-cerium oxide composite particles, a method for the preparation thereof and a resin composition and a cosmetic composition compounded therewith capable of exhibiting excellent transparency, stability and safety for human health along with a high ultraviolet shielding effect.

As is well known, ultraviolet rays cause degradation of plastic resins so that various measures have been proposed and undertaken heretofore.

As one of such measures, it is widely practiced that a plastic resin is admixed with a ultraviolet shielding agent including organic ultraviolet absorbers and inorganic ultraviolet scattering agents with an object to decrease the adverse influences of ultraviolet radiation. While the organic ultraviolet absorbers include salicylic acid derivatives, benzophenone derivatives, benzoyl triazole derivatives, cyanoacrylate derivatives and the like, these conventional ultraviolet absorbers have several problems to be solved relative to their insufficient heat resistance and low weatherability as well as toxicity of some decomposition products thereof against human body. With an object to solve these problems in organic ultraviolet absorbers, inorganic ultraviolet scattering agents, such as ultra fine particles of titanium dioxide and zinc oxide, have been developed and are under practical applications but they still have other problems to be solved relative to their dispersibility in matrix materials and catalytic activity to accelerate degradation of organic materials.

Ultraviolet light has an adverse influence also on human bodies. Namely, it is known that the so-called UV-B ultraviolet rays in the wavelength range of 280 to 320 nm cause cutaneous inflammations such as erythemas, vesicles and the like while the so-called UV-A ultraviolet rays in the wavelength range of 320 to 400 nm cause tanning of human skins by the accelerated formation of melanin. As a measure against these adverse influences of ultraviolet rays on the human skin, a great variety of sunscreen cosmetic or toiletry compositions have been developed heretofore. The conventional ultraviolet shielding agents compounded in these sunscreen cosmetic compositions can be grossly classified into two classes including ultraviolet absorbers such as cinnamic acid derivatives, benzophenone derivatives, dibenzoylmethane derivatives and the like and ultraviolet scattering agents such as zinc oxide, titanium dioxide and the like. The above mentioned ultraviolet absorbers, however, have several problems in respects of the relatively low ultraviolet absorptivity and safety against human body, in particular, when compounded in the cosmetic composition in a large amount. Further, the conventional ultraviolet scattering agents in a powder form have a problem that the cosmetic composition compounded therewith suffers a decrease in the transparency even with a substantial improvement in the dispersibility of the particles so that not only the users of the cosmetic composition feel a non-smooth and hard touch when the composition is applied to their skin but also the skin look is made unnatural.

Proposals have been made in recent years for the use of a cerium compound as an ultraviolet absorbing or scattering agent as is disclosed in Japanese Patent Kokai 6-145646 and 7-207251. This technology, however, is not fully practicable due to the incompatibility of requirements for an increase in the sunscreening power and transparency of the cosmetic composition compounded therewith as applied to the human skin so that it is eagerly desired to develop a novel cerium-based ultraviolet scattering agent improved in these respects.

SUMMARY OF THE INVENTION

The present invention accordingly has an object to provide a cerium-based ultraviolet shielding agent capable of exhibiting a high ultraviolet shielding power without decreasing the transparency of the composition compounded therewith and a method for the preparation thereof Another object of the invention is to provide a synthetic resin composition capable of exhibiting a high ultraviolet shielding effect as being compounded with the improved cerium-based ultraviolet shielding agent as well as a cosmetic or toiletry composition capable of exhibiting a high ultraviolet shielding effect without the problem of safety against human body and a degradation in the use feeling which the user of the cosmetic composition receives.

Namely, the present invention provides a powder of silica-cerium oxide composite particles as a composite of cerium oxide and amorphous silica contained in an amount of 5% to 60% by weight calculated as $SiO_2$.

Further, the invention provides a resin composition and a cosmetic composition compounded with the above mentioned silica-cerium oxide composite particles.

The silica-cerium oxide composite particles of the invention mentioned above can be prepared by the method which comprises the steps of:

(a) mixing an alkali with an aqueous solution of a cerium salt to precipitates cerium hydroxide in the form of an aqueous slurry;

(b) admixing the aqueous slurry containing the precipitates of cerium hydroxide with an aqueous solution of a silicate and an inorganic acid to precipitate amorphous silica in the aqueous slurry forming composite particles of amorphous silica and cerium hydroxide;

(c) separating the composite particles of amorphous silica and cerium hydroxide from the aqueous slurry; and (d) drying or calcining the composite particles.

DETAILED DESCRIPTION OF THE PREFERRED EMBODIMENTS

The silica-cerium oxide composite particles of the present invention can be obtained as a composite of cerium oxide with 5 to 60% by weight of amorphous silica, the balance being cerium oxide. The composite particles can be prepared by a method comprising the steps of: admixing an aqueous solution of a cerium salt with an alkali in an aqueous medium having a pH of 5 or higher and kept at a temperature not exceeding 60° C. to precipitate particles of cerium hydroxide -in the form of an aqueous slurry kept at a pH of 9 or higher; heating the aqueous slurry at 80° C. or higher; adding an aqueous solution of a water-soluble silicate such as sodium silicate and an inorganic acid to precipitate amorphous silica on the particles of cerium hydroxide; separating the particles from the aqueous medium; and drying or calcining the particles.

In the following, the procedure for the preparation of the inventive silica-cerium oxide composite particles is described step by step in more detail, of which the key steps are formation of cerium hydroxide and precipitation of amorphous silica thereon.

In the first place, an aqueous solution of a cerium salt is prepared by dissolving cerium carbonate in an inorganic acid such as hydrochloric acid and nitric acid or by dissolving cerium chloride or cerium nitrate in water. Though not particularly limitative, the concentration of the cerium salt in the aqueous solution should be high enough to facilitate precipitation of cerium hydroxide. The pH of the aqueous solution should be high enough provided that precipitation of cerium hydroxide does not take place. In the next place, the aqueous solution of the cerium salt and an alkaline aqueous solution of an alkali metal hydroxide such as sodium hydroxide and potassium hydroxide or ammonia water are introduced under agitation into water kept at a temperature not exceeding 60° C. and having a pH of 5 or higher or, preferably, 8 or higher so that particles of cerium hydroxide are precipitated to form an aqueous slurry.

Separately, an aqueous solution of sodium silicate is prepared by dissolving, for example, #3 water glass in water and a diluted aqueous solution of an inorganic acid such as hydrochloric, nitric and sulfuric acids is prepared. These aqueous solutions are introduced dropwise under agitation into the above prepared aqueous slurry of cerium hydroxide heated at a temperature of 80° C. or higher while the pH of the reaction mixture is kept at 9 or higher throughout so that precipitation of amorphous silica takes place. The amount of the sodium silicate introduced into the aqueous slurry is selected such that the amount thereof calculated as $SiO_2$ corresponds to 5 to 60% by weight based on the total amount of the cerium hydroxide calculated as $CeO_2$ and the sodium silicate calculated as $SiO_2$. The above mentioned conditions of the pH value and temperature are the key factors in order to ensure uniformity of the silica-cerium oxide composite particles.

In the next place, the thus obtained aqueous slurry of the composite particles is washed with water by decantation and the composite particles are recovered by filtration and dried and, if necessary, calcined followed by disintegration into a fine powder. It is optional that the wet cake of the composite particles separated from the aqueous slurry is dried and first disintegrated into a fine powder which is finally subjected to calcination.

Figure 1:
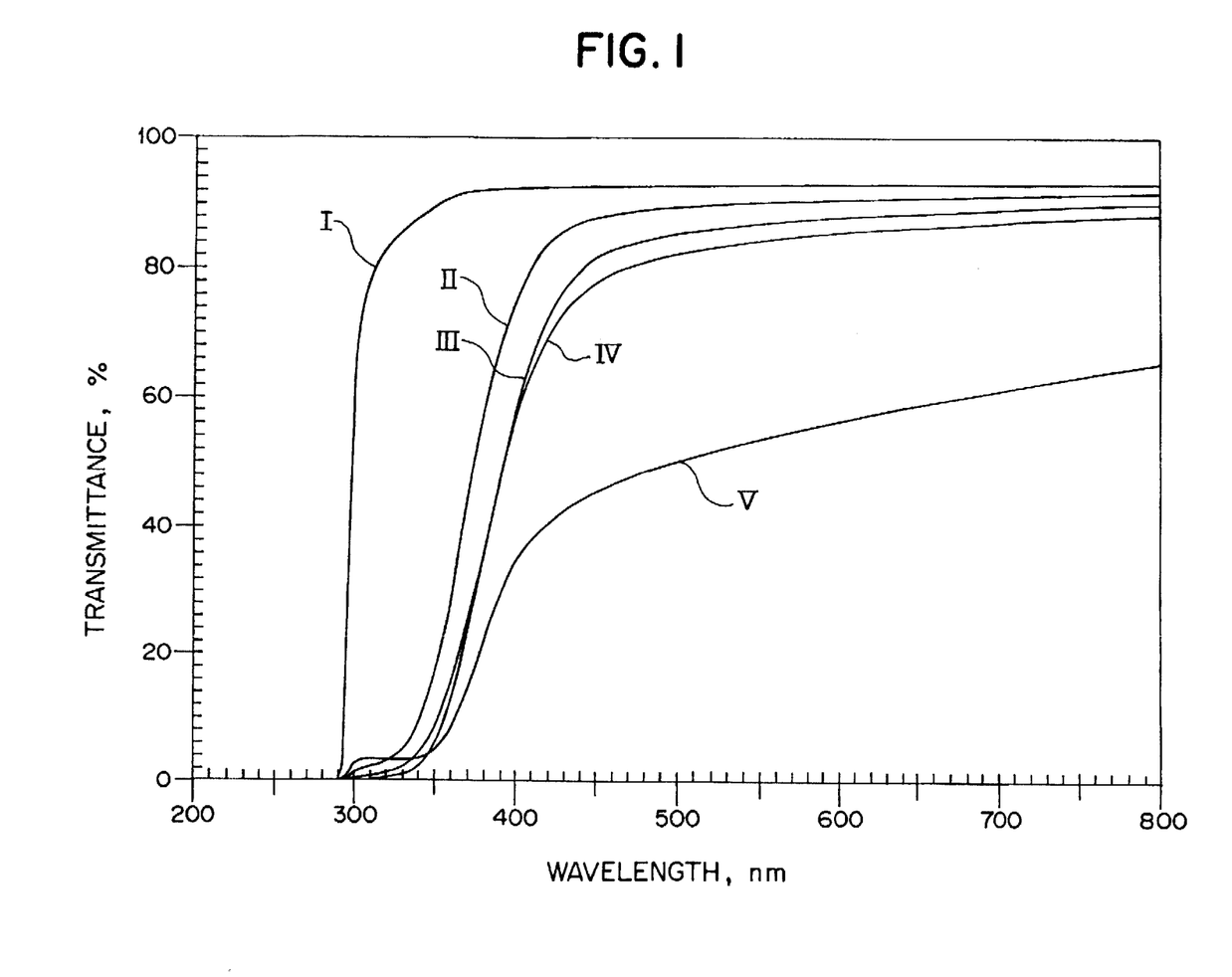
FIG. 1 shows the light transmittance of the silica-cerium oxide composite particles as a function of wavelength.

FIG. 1 of the accompanying drawing shows the light transmissivity of various grades of silica-cerium oxide composite particles measured by the procedure described below as a function of the wavelength, of which curve I is a control curve in the absence of any silica-cerium oxide composite particles, curve II is for silica-cerium oxide composite particles of which the content of silica is 50% by weight based on the total amount of silica and cerium oxide, curve III is for silica-cerium oxide composite particles of which the content of silica is 32% by weight, curve IV is for silica-cerium oxide composite particles of which the content of silica is 10% by weight and curve V is for a commercial product of cerium oxide $CeO_2$. As is understood from this figure, the cerium oxide powder shown by the curve V is inferior in the ultraviolet shielding effect in the wavelength range of 290 to 320 nm corresponding to the UV-B range and also has a low transmittance in the visible wavelength range from 400 to 800 nm. In contrast thereto, the silica-cerium oxide composite particles shown by the curves II, III and IV of which the content of silica is in the range from 5 to 60% by weight have an excellent ultraviolet shielding effect in the wavelength range of 290 to 320 nm and a high transmittance in the visible range of wavelength from 400 to 800 nm.

Figure 2:
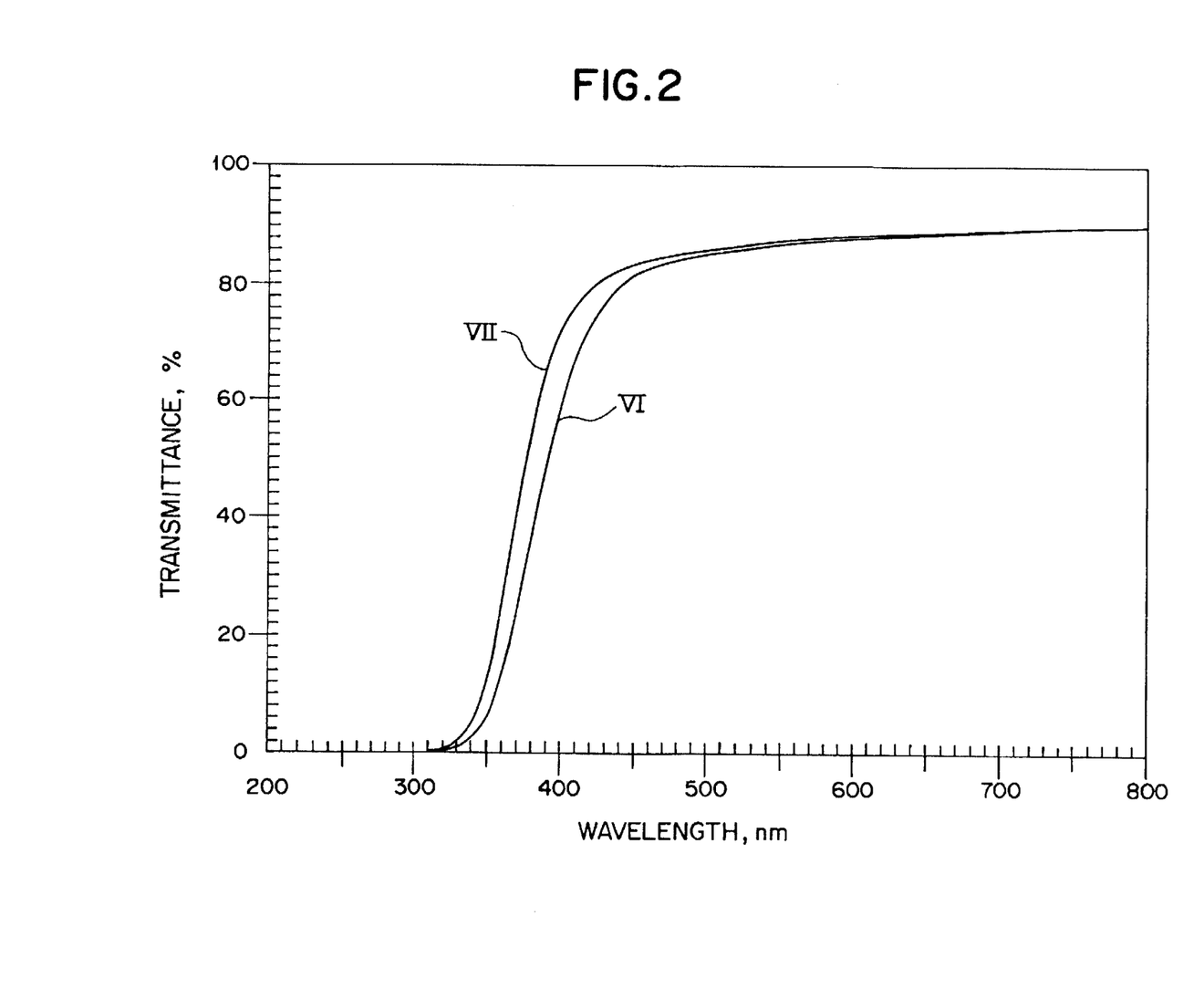
FIG. 2 shows the light transmittance of several kinds of silica-cerium oxide composite particles as dried and as calcined as a function of wavelength.

FIG. 2 shows the transmittance of the silica-cerium oxide composite particles, of which the content of silica is 32% by weight, as a function of wavelength. The curve VI is for the composite particles as dried and the curve VII is for the same composite particles dried and calcined at 500° C. Though not very significant, the curve VI shows somewhat better ultraviolet shielding effect than the curve VII in the wavelength range of 290 nm to 400 nm.

Figure 3:
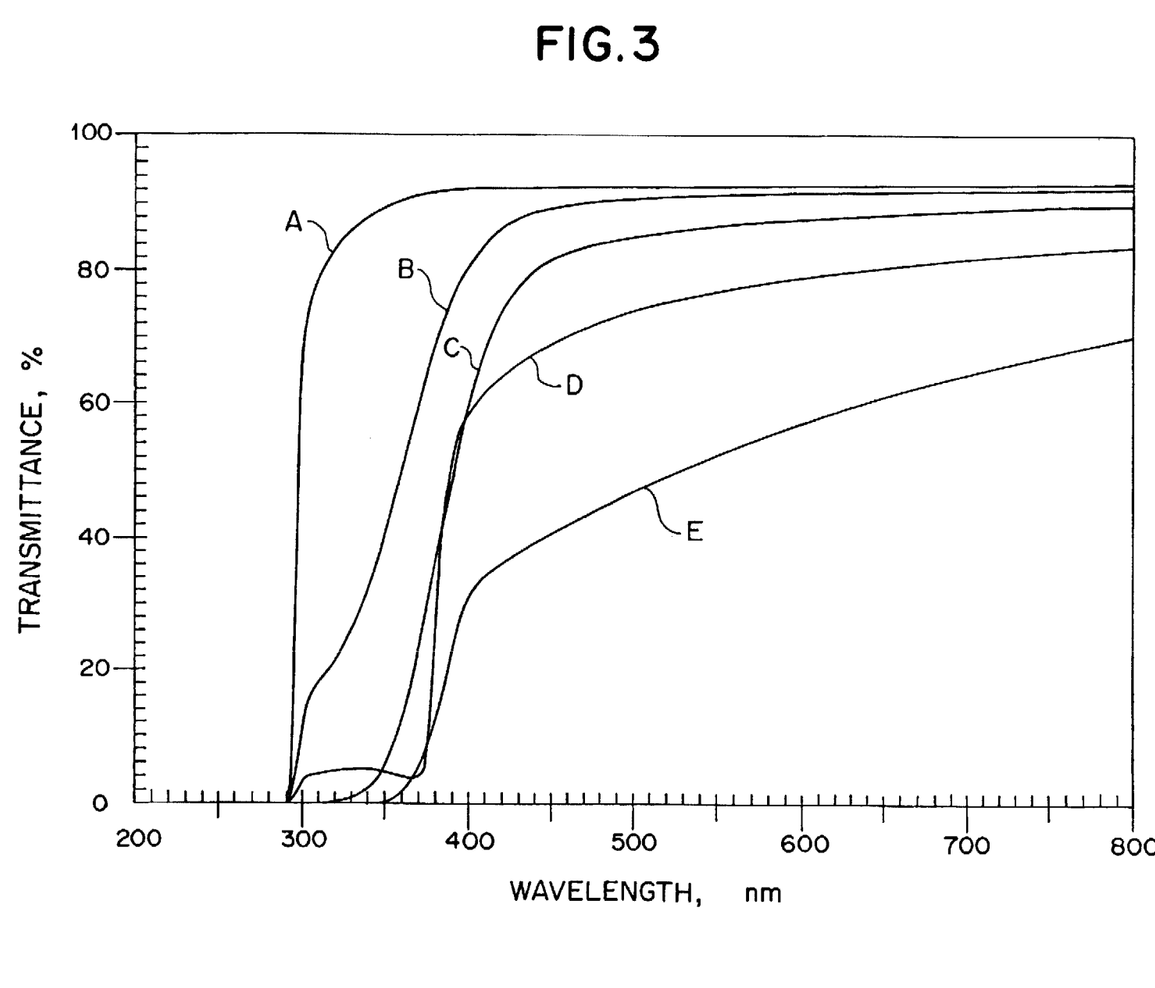
FIG. 3 is a graph showing the ultraviolet shielding effect and transparency of the inventive ultraviolet shielding agent in the visible region as a function of wavelength.

FIG. 3 shows the light transmittance of various kinds of inorganic ultraviolet shielding agents as a function of wavelength, in which curve A is without addition of any ultraviolet shielding agent for the purpose of blank test, curve B is for a synthetic silica-based ultraviolet shielding agent consisting of 24% by weight of cerium oxide and 76% by weight of silicon dioxide, curve C is for an inventive silica-cerium oxide composite particles containing 32% by weight of $SiO_2$, curve D is for fine particles of zinc oxide and curve E is for fine particles of titanium dioxide. It is understood from this figure that the inventive silica-cerium oxide composite particles containing 32% by weight of $SiO_2$ have a high ultraviolet shielding effect and high transmittance in the visible region as compared with conventional ultraviolet shielding agents.

The measuring method for the above given light transmittance shown in FIGS. 1 to 3 was as follows. Thus, the sample powder of the ultraviolet shielding agent was added to and dispersed in 0.4 ml of castor oil in such an amount that the content thereof was 3.0% by weight after drying by using a Hoover muller rotating at 50 revolutions×2 and the blend was further dispersed with addition of 6 ml of a clear lacquer. A transparent fused silica glass plate coated with the thus prepared liquid dispersion in a thickness of 30 μm was subjected to the measurement of the light transmittance on a spectrophotometer (Model UV-2200, manufactured by Shimadzu Seisakusho Co.).

Following is a description of the plastic resin composition and a cosmetic composition according to the invention.

As is known, resin compositions in general are subject to degradation when exposed to ultraviolet rays. This adverse influence of ultraviolet rays can be prevented or reduced by compounding the resin composition with the silica-cerium oxide composite particles of the present invention. A layer of a coating composition containing the silica-cerium oxide composite particles of the invention dispersed therein has an effect to prevent or decrease the photodegradation of various articles coated therewith.

The resin composition implied here includes not only those molding compositions based on a plastic resin as the principal ingredient including synthetic resins such as polyvinyl chloride, polypropylene and polycarbonate and natural resins but also various types of coating compositions containing these resins as a vehicle.

The cosmetic composition according to the invention exhibits excellent transparency and high sunscreening effect on the human skin by virtue of the inventive silica-cerium oxide composite particles compounded therein. The formulation types of the inventive cosmetic or toiletry composition include skin-care toiletry compositions such as milk lotions, skin lotions and the like, cosmetics such as foundations, lipsticks, face powders and the like, hair treatment compositions and so on while the advantage of the invention relative to cosmetic compositions is most remarkable in sunscreen compositions. The amount of the inventive silica-cerium oxide composite particles in the cosmetic or toiletry composition is usually in the range from 0.1 to 70% by weight though dependent on various factors.

It is optional that the silica-cerium oxide composite particles are subjected to a surface treatment before compounding in a cosmetic composition. The surface treatment agents used here include metal soaps, silicones, dialkyl phosphoric acids, perfluoroalkyl group-containing compounds, amino acids, lecithin, collagen and the like.

The sunscreening effect exhibited by the inventive cosmetic composition can be further enhanced by compounding the composition with other known ultraviolet absorbers and/or ultraviolet scattering agents in combination with the inventive silica-cerium oxide composite particles. The ultraviolet absorber suitable for the purpose includes oxybenzone, octyl methoxycinnamate, 4-tert-butyl-4'-methoxy benzoylmethane and the like either singly or as a combination of two kinds or more according to need. The compounding amount thereof is, though not particularly limitative, usually in the range from 0.1 to 40% by weight of the composition. The ultraviolet scattering agent used for the above mentioned purpose is preferably a fine powder of titanium dioxide or zinc oxide, more preferably, having an average particle diameter not exceeding 0.05 µm. The compounding amount thereof is preferably in the range from 0.1 to 50% by weight.

It is of course optional that the cosmetic composition of the invention is further admixed with various kinds of known adjuvants conventionally used in cosmetic compositions including cosmetic powders, surface active agents, oleaginous agents, gelation agents, polymeric compounds, aesthetic ingredients, moisturizing agents, coloring agents, preservatives, perfumery and so on each in a limited amount not to decrease the advantages obtained by the invention.

In the following, the invention is illustrated in more detail by way of Examples.

EXAMPLE 1

A first aqueous solution in a volume of 3.3 liters was prepared by dissolving 488 g of cerium chloride $CeCl_3$ in water. Separately, a second aqueous solution in a volume of 3.3 liters was prepared by dissolving 237 g of sodium hydroxide NaOH in water. Into 8.5 liters of water kept at a temperature of 30° to 40° C. under agitation were added dropwise the first aqueous solution of cerium chloride and the second aqueous solution of sodium hydroxide concurrently while the pH of the reaction mixture was kept in the range from 9 to 11 and the temperature of the reaction mixture was kept at a temperature not exceeding 50° C. After completion of the dropwise addition of the two aqueous solutions, agitation of the reaction mixture was further continued for 30 minutes and the pH of the reaction mixture was again adjusted to be 5 or higher. The precipitates of cerium hydroxide in the thus obtained aqueous slurry were washed five times with water by decantation to obtain an aqueous slurry freed from dissolved solutes.

Separately, a third aqueous solution of sodium silicate in a volume of 2 liters was prepared by dissolving 562 g of a water glass, of which the content of $SiO_2$ was 28.5% by weight, in water and 2 liters of a diluted sulfuric acid was prepared by diluting 75.8 g of 95% sulfuric acid with water. Into the aqueous slurry of cerium hydroxide kept at a temperature of 80° C. or higher under agitation, the sodium silicate solution and the diluted sulfuric acid were concurrently introduced dropwise at such rates that the pH of the reaction mixture was kept at 9 or higher throughout. After completion of the dropwise addition of the two solutions, agitation of the reaction mixture was continued for additional 30 minutes and the pH of the reaction mixture was adjusted to be 7 to 8 by the addition of the diluted sulfuric acid. The thus obtained aqueous slurry was filtered to collect the precipitates which were washed with water, dried and disintegrated into fine silica-cerium oxide composite particles of which the content of silica as $SiO_2$ was 32% by weight.

EXAMPLE 2

A plasticized polyvinyl chloride resin was compounded with 0.5% by weight, 1.0% by weight or 2.0% by weight of the silica-cerium oxide composite particles containing 32% by weight of silica $SiO_2$ as obtained in Example 1 as an ultraviolet shielding agent. The polyvinyl chloride resin as such and the three resin compounds blended with varied amounts of the particles were each shaped into a sheet having a thickness of 0.23 mm by using hot calendering rollers.

Figure 4:
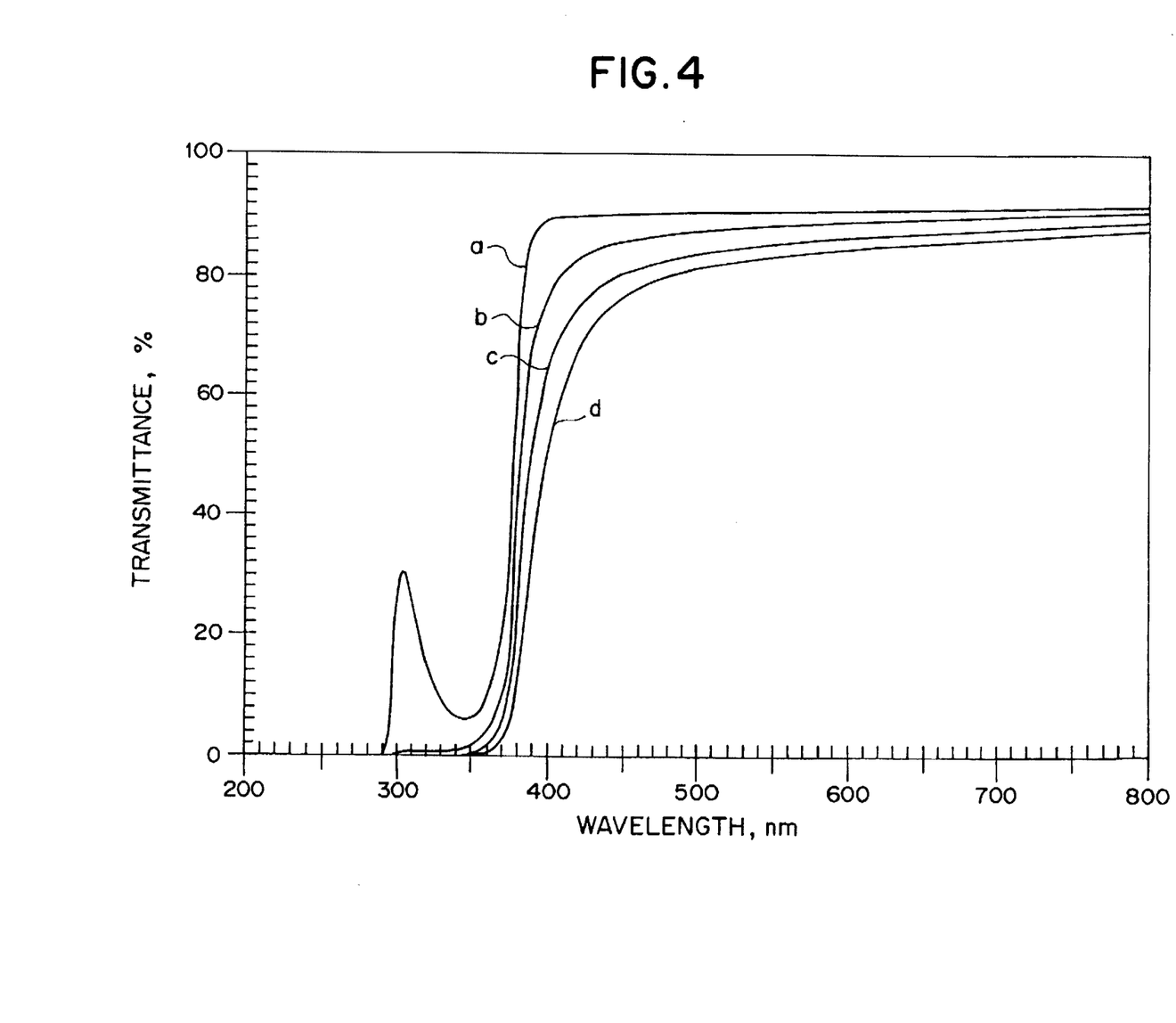
FIG. 4 shows the light transmittance of the plastic resin sheets obtained in Example 2 as a function of wavelength.

Each of the thus prepared four resin sheets was subjected to the measurement of the transmittance on a spectrophotometer (Model UV-2200, manufactured by Shimadzu Seisakusho Co.) to give the results shown in FIG. 4, in which the curve a is for the resin without the silica-cerium oxide composite particles and curves b, c and d are for the resin compositions containing 0.5%, 1.0% and 2.0%, respectively, by weight of the silica-cerium oxide composite particles. This figure indicates that, while the ultraviolet shielding effect of the resin sheet can be increased by increasing the compounded amount of the inventive silica-cerium oxide composite particles, the transmittance of the resin films in the visible region is little affected by the increase in the amount of the composite particles.

EXAMPLE 3

A cream foundation was prepared in the following formulation including the inventive silica-cerium oxide composite particles containing 32% by weight of $SiO_2$ as prepared in Example 1 by the method described below.

| Formulation: | | |
|---|---|---|
| (1) | Stearic acid | 5.0%bywt. |
| (2) | Oleophilic glycerin monostearate | 2.5 |
| (3) | Cetanol | 1.5 |
| (4) | Isopropyleneglycol monolaurate | 2.5 |
| (5) | Liquid paraffin | 8.0 |
| (6) | Isopropyl myristate | 7.0 |
| (7) | Propyl p-oxybenzoate | 0.1 |
| (8) | Purified water | 47.3 |
| (9) | Triethanolamine | 1.2 |
| (10) | Sorbitol | 3.0 |
| (11) | Methyl p-oxybenzoate | 0.2 |
| (12) | Titanium dioxide | 8.0 |
| (13) | Kaolin | 5.0 |
| (14) | Silica-cerium oxide composite particles | 3.0 |
| (15) | Bentonite | 1.0 |
| (16) | Red iron oxide | 2.5 |

| (17) | Yellow iron oxide | 2.0 |
|---|---|---|
| (18) | Black iron oxide | 0.2 |
| | Total | 100.0 |

Preparation Method (a) The ingredients (12) to (14) and (16) to (18) were thoroughly blended together.

(b) The ingredient (15) was admixed with (8) heated at 80° C. to effect full swelling thereof into which the ingredients (9) to (11) were added and dissolved therein followed by the addition of the blend prepared in (a) above at 80° C. to be dissolved therein (aqueous phase).

(c) The ingredients (1) to (7) were mixed together at 80° C. (oily phase).

(d) The aqueous phase prepared in (b) and the oily phase prepared in (c) were mixed together to be emulsified followed by cooling down to 35° C. under agitation.

The cream foundation obtained with the above given formulation and in the above described preparation method exhibited excellent transparency on the human skin along with good spreadability and an excellent sunscreening effect.

PREPARATION EXAMPLE 1

Into a flask were taken 150 g of the silica-cerium oxide composite particles prepared in Example 1 and 200 g of purified water, and they were mixed together and heated up to 70° C. to prepare an aqueous slurry, which was further admixed gradually with an aqueous emulsion obtained from 6 g of diethanolamine salt of perfluoroalkyl phosphoric acid ester (Asahiguard AG 530, a product by Asahi Glass Co.) and 150 g of purified water followed by agitation continued for 1 hour. After acidification, the aqueous dispersion was washed with water and filtered to collect the particles which were dried to give 154 g of fluorinated silica-cerium oxide composite particles, referred to as the fluorinated composite particles hereinafter.

PREPARATION EXAMPLE 2

Into a flask were taken 150 g of the silica-cerium oxide composite particles prepared in Example 1 and 150 g of isopropyl alcohol and they were mixed together and heated up to 70° C. to give a mixture, which was further admixed with 3 g of a methyl hydrogen polysiloxane (a product by Shin-Etsu Chemical Co.) and mixed together for 1 hour followed by removal of isopropyl alcohol by heating under reduced pressure to give 152 g of silicone-treated silica-cerium oxide composite particles, referred to as the silicone-treated composite particles hereinafter.

EXAMPLE 4

A sunscreen milk lotion was prepared by using the fluorinated composite particles obtained in Preparation Example 1 described above according to the following formulation.

| Formulation: | | |
|---|---|---|
| (1) | Fluorinated composite particles | 10.0%bywt. |
| (2) | Microcrystalline wax | 1.0 |
| (3) | Beeswax | 2.0 |
| (4) | Squalane | 10.0 |
| (5) | Methylpolysiloxane (10 cSt) | 10.0 |
| (6) | Decamethyl cyclopentasiloxane | 10.0 |
| (7) | Sorbitan sesquioleate | 4.0 |
| (8) | Polyoxyethylene-methylpolysiloxane copolymer | 1.0 |
| (9) | Oxybenzone | 0.1 |
| (10) | 1,3-Butyleneglycol | 9.0 |
| (11) | Preservative | q.s. |
| (12) | Purified water | balance |
| (13) | Perfume | q.s. |
| | Total | 100.0 |

Preparation Method (a) The ingredients (2) to (9) were melted together by heating up to 70° C. followed by the admixture of the ingredient (1).

(b) The ingredients (10) to (12) were mixed together by heating up to 70° C. and this mixture was added to the mixture prepared in (a) above to be emulsified.

(c) The emulsion obtained in (b) above was, after cooling, admixed with the ingredient (13) to give a sunscreen milk lotion.

COMPARATIVE EXAMPLE 1

A comparative sunscreen milk lotion was prepared according to the same formulation and in the same preparation method as in Example 4 above except for the replacement of the ingredient (1) with the same amount of ultra fine particles of titanium dioxide.

When applied to the human skin, this comparative milk lotion exhibited a pale-white color and white powderiness not to give a natural feeling of cosmetic finish. In contrast thereto, the milk lotion prepared in Example 4 could exhibit a transparent and good cosmetic finish along with an excellent sunscreening effect.

EXAMPLE 5

A powder foundation was prepared by using the silicone-treated composite particles obtained in Preparation Example 2 described above according to the following formulation and in the preparation method described below.

| Formulation: | | |
|---|---|---|
| (1) | Silicone-treated talc | 20.0%bywt. |
| (2) | Silicone-treated mica | balance |
| (3) | Silicone-treated titanium dioxide | 12.0 |
| (4) | Silicone-treated red iron oxide | 1.0 |
| (5) | Silicone-treated yellow iron oxide | 3.0 |
| (6) | Silicone-treated black iron oxide | 0.1 |
| (7) | Silicone-treated composite particles | 20.0 |
| (8) | Silicone-treated zinc oxide | 1.0 |
| (9) | Squalane | 5.0 |
| (10) | Tri(2-ethylhexanoic acid) glyceryl | 2.0 |
| (11) | White Vaseline | 1.0 |
| (12) | Preservative | q.s. |
| (13) | Perfume | q.s. |
| | Total | 100.0 |

Preparation Method (a) The ingredients (1) to (8) were blended together by using a Henschel mixer.

(b) The ingredients (9) to (11) were mixed together by heating to give a mixture which was admixed with the blend prepared in (a) above followed by the addition of the ingredients (12) and (13).

(c) The mixture obtained in (b) above was pulverized into a powder which was compacted by compression to give a powder foundation.

COMPARATIVE EXAMPLE 2

A comparative powder foundation was prepared in the same formulation and in the same preparation method as in Example 5 except for the replacement of the silicone-treated composite particles as the ingredient (7) with the same amount of ultra fine particles of titanium dioxide.

When applied to the human skin, this comparative powder foundation exhibited a pale-white color and white powderiness not to give a natural feeling of cosmetic finish. In contrast thereto, the powder foundation prepared in Example 5 could exhibit a transparent and good cosmetic finish along with an excellent sunscreening effect.

EXAMPLE 6

A lipstick was prepared by using the silica-cerium oxide composite particles containing 32% by weight of $SiO_2$ obtained in Preparation Example 1 described above according to the following formulation and in the preparation method described below.

| Formulation: | | |
|---|---|---|
| (1) | Ethylene-propylene copolymer | 9.0%bywt. |
| (2) | Microcrystalline wax | 5.0 |
| (3) | Candelilla wax | 3.0 |
| (4) | Ceresin wax | 3.0 |
| (5) | Lanolin | 10.0 |
| (6) | Castor oil | 20.0 |
| (7) | Isocetyl octanoate | 26.9 |
| (8) | D & C Red No. 6 | 2.0 |
| (9) | D & C Red No. 7 | 1.0 |
| (10) | D & C Orange No. 5 | 0.1 |
| (11) | Silica-cerium oxide composite particles | 20.0 |
| | Total | 100.0 |

Preparation Method (a) The ingredients (8) to (11) were blended together with addition of a part of the ingredient (6) and they were mixed on a mixing roller.

(b) The ingredients (1) to (5) and (7) and the remaining part of the ingredient (6) were melted together by heating followed by the addition of the mixture obtained in (a) above to give a uniform mixture.

(c) A casing for lipstick is filled with the molten mixture prepared in (b) above followed by cooling to give an encased lipstick.

COMPARATIVE EXAMPLE 3

A comparative lipstick was prepared in the same formulation and in the same preparation method as in Example 6 described above except for the replacement of the silica-cerium oxide composite particles with the same amount of ultra fine particles of titanium dioxide.

When applied to a human lip, this lipstick exhibited unnatural, pale coloring not to give healthy feeling of the lip finishing, while the lipstick prepared in Example 6 could give a feeling of transparency with healthy coloration along with an excellent sunscreening effect.

EXAMPLE 7

A pressed powder was prepared by using the silica-cerium oxide composite particles containing 32% by weight of $SiO_2$ obtained in Preparation Example 1 described above according to the following formulation and in the preparation method described below.

| Formulation: | | |
|---|---|---|
| (1) | Silica-cerium oxide composite particles | 50.0%bywt. |
| (2) | Talc | 30.0 |
| (3) | Sericite | 6.0 |
| (4) | Kaolin | balance |
| (5) | Titanium dioxide | 3.0 |
| (6) | Zinc myristate | 2.0 |
| (7) | Red iron oxide | 0.2 |
| (8) | Yellow iron oxide | 0.8 |
| (9) | Squalane | 2.0 |
| (10) | Octyl methoxycinnamate | 2.0 |
| (11) | Preservative | q.s. |
| (12) | Perfume | q.s. |
| | Total | 100.0 |

Preparation Method (a) The ingredients (1) to (8) were blended together to give a mixture.

(b) The ingredients (9) to (12) were mixed together and added to the mixture obtained in (a) above to give a uniform mixture.

(c) The mixture obtained in (b) is pulverized and the powder is compression-molded to give a pressed powder.

COMPARATIVE EXAMPLE 4

A comparative pressed powder was prepared in the same formulation and in the same preparation method as in Example 7 described above except for the replacement of the silica-cerium oxide composite particles with the same amount of ultra fine titanium dioxide particles.

When applied to a human skin, this comparative face powder exhibited paleness with whitish powderiness not to give natural feeling of cosmetic finish while the face powder prepared in Example 7 could give a good feeling of cosmetic finish with transparency along with an excellent sunscreening effect.

What is claimed is:

1. Silica-cerium oxide composite particles as a composite of cerium oxide and amorphous silica of which the content of silica is in the range from 5 to 60% by weight calculated as $SiO_2$ based on the total amount of silica and cerium oxide.

2. A method for the preparation of silica-cerium oxide composite particles which comprises the steps of:

(a) adding an aqueous alkaline solution to an aqueous solution of cerium salt to precipitate cerium hydroxide in the form of an aqueous slurry;

(b) adding, to the aqueous slurry containing the precipitates of cerium hydroxide, an aqueous solution of a water-soluble silicate and an inorganic acid to give composite particles of silica and cerium hydroxide in the form of an aqueous slurry;

(c) separating the composite particles from the aqueous slurry; and (d) drying or calcining the composite particles.

3. The method for the preparation of silica-cerium oxide composite particles as claimed in claim 2 in which the cerium salt is cerium chloride or cerium nitrate.

4. The method for the preparation of silica-cerium oxide composite particles as claimed in claim 2 in which addition of an aqueous alkaline solution to the aqueous solution of a cerium salt in step (a) is performed by the introduction of an aqueous solution of an alkali metal hydroxide or ammonia water and the aqueous solution of the cerium salt into an aqueous medium kept at a temperature not exceeding 60° C. by keeping the pH of the aqueous medium at 5 or higher.

5. The method for the preparation of silica-cerium oxide composite particles as claimed in claim 2 in which the water-soluble silicate used in step (b) is a sodium silicate.

6. The method for the preparation of silica-cerium oxide composite particles as claimed in claim 2 in which the inorganic acid used in step (b) is selected from the group consisting of hydrochloric acid, nitric acid and sulfuric acid.

7. The method for the preparation of silica-cerium oxide composite particles as claimed in claim 5 in which the amount of the sodium silicate is in the range from 5% to 60% by weight calculated as $SiO_2$ based on the total amount of the cerium hydroxide calculated as $CeO_2$ and the sodium silicate calculated as $SiO_2$.

8. A method for imparting a resin composition with ultraviolet ray shieldability which comprises admixing the resin composition with a powder of silica-cerium oxide composite particles as a composite of cerium oxide and amorphous silica of which the content of silica is in the range from 5 to 60% by weight based on the total amount of the silica calculated as $SiO_2$ and cerium oxide calculated as $CeO_2$.

9. A method for imparting a cosmetic composition with a sunscreening effect which comprises admixing the cosmetic composition with a powder of silica-cerium oxide composite particles as a composite of cerium oxide and amorphous silica of which the content of silica is in the range from 5 to 60% by weight based on the total amount of the silica calculated as $SiO_2$ and cerium oxide calculated as $CeO_2$.

10. The method for imparting a cosmetic composition with a sunscreening effect as claimed in claim 9 in which the silica-cerium oxide composite particles are surface-treated with a silicone.

11. The method for imparting a cosmetic composition with a sunscreening effect as claimed in claim 9 in which the silica-cerium oxide composite particles are surface-treated with a compound having a perfluoroalkyl group in the molecule.

12. The method for imparting a cosmetic composition with a sunscreening effect as claimed in claim 9 in which the cosmetic composition is compounded with the silica-cerium oxide composite particles in combination with an ultraviolet absorber or an ultraviolet scattering agent.

13. The method for imparting a cosmetic composition with a sunscreening effect as claimed in claim 12 in which the ultraviolet absorber is selected from the group consisting of oxybenzone, octyl methoxycinnamate and 4-tert-methyl-4'-methoxybenzoyl methane.

14. The method for imparting a cosmetic composition with a sunscreening effect as claimed in claim 12 in which the content of the ultraviolet absorber in the cosmetic composition is in the range from 0.1% to 40% by weight.

15. The method for imparting a cosmetic composition with a sunscreening effect as claimed in claim 12 in which the ultraviolet scattering agent is titanium dioxide or zinc oxide.

16. The method for imparting a cosmetic composition with a sunscreening effect as claimed in claim 12 in which the content of the ultraviolet scattering agent in the cosmetic composition is in the range from 0.1% to 50% by weight.

17. The method for imparting a cosmetic composition with a sunscreening effect as claimed in claim 9 in which the amount of the silica-cerium oxide composite particles is in the range from 0.1% to 70% by weight based on the amount of the cosmetic composition.

* * * * *